US00PP22469P2

(12) United States Plant Patent
Carruth

(10) Patent No.: US PP22,469 P2
(45) Date of Patent: Jan. 31, 2012

(54) CLIMBING ROSE PLANT NAMED 'WEKSPITRIB'

(50) Latin Name: *Rosa hybrida*
Varietal Denomination: WEKspitrib

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/927,567

(22) Filed: Nov. 18, 2010

(51) Int. Cl.
*A01H 5/00* (2006.01)

(52) U.S. Cl. ..... Plt./109

(58) Field of Classification Search ..... Plt./109
See application file for complete search history.

*Primary Examiner* — Kent L Bell

(74) *Attorney, Agent, or Firm* — McKee, Voorhees & Sease, P.L.C.

(57) ABSTRACT

A new variety of Climbing rose suitable for garden decoration, having flowers of wine purple striped with bright white coloration.

1 Drawing Sheet

Classification: The present invention relates to a new *Rosa hybrida* plant.

Variety denomination: The new plant has the varietal denomination 'WEKspitrib'.

BACKGROUND OF THE INVENTION

This invention relates to a new and distinct variety of Climbing Rose. It has as its seed parent the variety known as 'WEKbecfoj' (U.S. Plant Pat. No. 18,033) and as its pollen parent the variety known as 'FRAntasia' (U.S. Plant Pat. No. 17,518).

SUMMARY OF THE INVENTION

Among the features which distinguish the new variety from other presently available and commercial rose cultivars known to the inventor are the following combinations of characteristics: its hairs on the receptacle of the flower and on the hip surface, its hairs on the under surface of the mature and young leaflet veins and on the edge of the serrated margin and its very unusual wine purple striped with bright white flower coloration. The plant has a spreading climbing growth habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKspitrib' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKbecfoj' by the following combination of characteristics: whereas 'WEKspitrib' bears semi-double flowers (about 8 to 12 petals) of wine purple striped with bright white coloration, 'WEKbecfoj' bears single flowers of irregularly striped and flecked pastel pink and yellow coloration with significantly lesser petalage (about 5 to 7 petals).

The new variety may be distinguished from its pollen parent, 'FRAntasia' by the following combination of characteristics: whereas 'WEKspitrib' bears semi-double flowers (about 8 to 12 petals) of wine purple striped with bright white coloration, 'FRAntasia' bears semi-double flowers of purple-blue coloration with significantly heavier petalage (about 13 to 17 petals). The new variety is classified as a climbing rose with a spreading climbing growth habit with canes about 300 cm. to about 350 cm. in length, whereas the pollen parent is classified as a shrub rose with a significantly shorter very upright growing habit (about 175 to about 210 cm. in height).

COMPARISON WITH THE CLOSEST COMMERCIALLY AVAILABLE CULTIVAR

The new variety may be distinguished from its closest commercially available cultivar, 'JACpurr' (not patented) by the following combination of characteristics: whereas 'WEKspitrib' bears semi-double flowers (about 8 to 12 petals) of wine purple striped with bright white coloration, 'JACpurr' bears double flowers of purple mauve streaks with white flecks coloration with significantly heavier petalage (about 40 petals). The new variety is classified as a climbing rose with a spreading climbing growth habit with canes about 300 cm. to about 350 cm. in length, whereas the closest commercially available cultivar is classified as a floribunda rose with a significantly shorter upright growth habit (about 75 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of October. Phenotypic expression may vary with environmental, cultural and climatic conditions, as well as differences in conditions of light and soil.

FLOWER

The new variety usually bears its flowers in clusters of five to fifteen or more per stem. Flowers are sometimes borne in rounded inflorescences but usually borne in racemes on strong medium to long stems (about 30 to about 120 cm.). Outdoors, the plant blooms abundantly and nearly continuously during the growing season. The flowers have a moderate to strong sweet spicy fragrance.

BUD

The peduncle is about 3.4 to about 4.7 cm. in length, of slender to average caliper (about 0.3 to about 0.4 cm. in diameter), and usually erect to somewhat bending. It is almost entirely smooth, with very few stipitate glands and some hairs. Peduncle color is between 144A and 147B.

Before the calyx breaks, the bud is about 1.1 to about 1.4 cm. in diameter at the widest point, about 2.0 to about 2.5 cm. in length, and pointed to ovoid in shape. The surface of the bud bears between 3 to 6 foliaceous appendages and some stipitate glands, usually with slender entire foliaceous parts extending beyond the tip of the bud about ¼ or more of its length. Bud color is between 146B and 146C.

The sepals are about 2.4 to about 2.7 cm. in length and about 0.7 to about 1.0 cm. in width at the widest point. The outer surface color of the sepal is between 146B and 146C. The inner surface color of the sepal is near 144A broadly bordered by near 147A. The inner surface of the sepal is covered with fine wooly tomentum; sepal margins are lined with few stipitate glands and many hairs.

The receptacle of the flower is of medium length (about 0.3 to about 0.5 cm.) and average in caliper (about 0.6 to about 0.7 cm. in diameter). The receptacle is somewhat ovoid to globular in form. Its surface is very smooth with few stipitate glands and some hairs. The receptacle color is between 146B and 146C.

As the petals open (after the calyx breaks), the bud is about 1.5 to about 1.7 cm. in diameter at the widest point, about 2.5 to about 2.8 cm. in length, and very pointed to somewhat ovoid in form. The color of the under surfaces of the newly opened petals is sometimes irregularly striped and flecked with as dark as between 185B and 59C to as light as near 155B. At the point where the petal attaches, there is a moderately large zone of between 4D and 2D, suffusing into the petal with near 157C.

The striping and flecking occur with a higher incidence on the upper surface than the under surface.

The color of the upper surfaces of the newly opened petals is often irregularly striped and flecked with as dark as between 187A and 187B to as light as near 155B to sometimes suffused with between 186B and 186C. At the point where the petal attaches, there is a moderately large zone of near 3A, suffusing into the petal with between 4C and 3C.

BLOOM

When fully open, the bloom ranges from about 6.5 to about 9 cm. in diameter. Petalage is semi-double with about 8 to 12 petals and about 1 to 3 petaloids irregularly arranged. When partially open, the bloom form is somewhat cupped, and the petals are moderately loosely spiraled to cupped with petal edges very slightly reflexed outward. When fully open, the bloom form is more flat to lightly cupped, and the petals are more flat to undulated with petal edges very slightly reflexed outward.

PETALS

The substance of the petals is moderately heavy and of medium thickness, with upper surfaces somewhat velvety and under surfaces somewhat shiny to satiny. The petals are about 3.3 to about 3.9 cm. in length and about 3.9 to about 4.6 cm. in width at the widest point. Petal margins are mostly entire, sometimes slightly notched.

The outer petals are very broadly obovate in shape with moderately rounded apices.

The inner petals are somewhat round with somewhat rounded apices.

Petaloids are about 2.3 to about 2.8 cm. in length and about 1.2 to about 1.7 cm. in width at the widest point. Petaloids are shaped irregularly to somewhat oblanceolate with moderately rounded apices.

NEWLY OPENED FLOWER

The under surface color of the outer, intermediate and inner petals is sometimes irregularly striped and flecked with as dark as between 64B and 67A to as light as between 155B and 69D sometimes suffused with between 63D and 68D. At the point where the petal attaches, there is a moderately large zone of near 4D, suffusing into the petal with near 65D.

The upper surface color of the outer, intermediate and inner petals is often irregularly striped and flecked with between 59A and darker than 61A to as light as near 155B sometimes suffused with between 64C and 70B. At the point where the petal attaches, there is a moderately large zone of near 4B suffusing into the petal with near 155B.

The under and upper surface color of the petaloids are similar in coloration to the upper and under surfaces of the intermediate and inner petals.

The striping and flecking occur with a higher incidence on the upper surface than the under surface.

The general tonality of the newly opened flower is often irregularly striped and flecked with between 59A and darker than 61A to as light as near 155B sometimes suffused with between 64C and 70B showing a moderately large central eye zone of near 155B.

THREE-DAY-OLD FLOWER

The under surface color of the outer, intermediate and inner petals is sometimes irregularly striped and flecked with as dark as between 64B and 64C to as light as between 155B and 69D. At the point where the petal attaches, there is a moderately large zone of near 69D.

The upper surface color of the outer, intermediate and inner petals is often irregularly striped and flecked with between 71A and darker than 71A to as light as near 155B sometimes suffused with between 72C and 70B. At the point where the petal attaches, there is a moderately large zone of between 69D and 155B.

The under and upper surface color of the petaloids are similar in coloration to the upper and under surfaces of the intermediate and inner petals.

The striping and flecking occur with a higher incidence on the upper surface than the under surface.

The general tonality of the three-day-old flower is often irregularly striped and flecked with between 71A and darker than 71A to as light as near 155B sometimes suffused with between 72C and 70B showing a moderately large central eye zone of between 69D and 155B.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 50) and are arranged regularly about the pistils. The filaments are of somewhat short to medium length (about 0.4 to about 0.7 cm.) most with anthers. Filaments are between 14C and 9C in color. The anthers are somewhat small for the class and all open approximately at the same time. Anther color when immature is near 14A. Anther color at maturity is between 163A and 165A. Pollen is somewhat abundant and near 14D in color.

FEMALE REPRODUCTIVE ORGANS

Pistils vary in number (average about 35). The styles are somewhat uneven, average to long in length (about 0.4 to about 0.8 cm.), somewhat thin to average in caliper, and moderately bunched. Stigma color is near 4B. Style color is near 2D. Ovaries are usually all enclosed in the calyx.

Hips are moderately short in length (about 0.9 to about 1.2 cm.), rounded and flat at the top, and between 25A and 28B in color when ripe. The hip surface is smooth with some hairs and with thick fleshy walls. The sepals are moderately permanent, and usually straight in shape.

The seeds are irregularly rounded, smooth in texture, approximately 3 to about 9 per hip, about 0.3 to about 0.5 cm. in diameter at the widest point and between 162C and 161C in color.

FOLIAGE

The compound leaves are usually comprised of three to seven leaflets and are borne abundantly. The seven-leaflet leaves are about 9.4 to about 15.0 cm. in length and about 5.7 to about 10.9 cm. in width at the widest point, moderately heavy to somewhat crisp in texture, and glossy in finish on the upper side of the new leaf, semi-glossy to almost matte in finish on the upper side of the mature leaf. The under side finish of the mature leaf is matte. Often on the under surface of the mature leaf and the young leaf some hairs can be observed mostly on the leaflet veins and on the edge of the serrated margin. The terminal leaflets are about 3.2 to about 7.5 cm. in length and about 2.2 to about 5.0 cm. in width at the widest point, shaped ovate to somewhat rounded with acute to somewhat acuminate apices and rounded bases. Their margins are usually simply serrate.

The upper surface color of the mature leaf is between 147A and 137A. The under surface color of the mature leaf is between 147B and 146B. The upper surface color of the young leaf is between 139A and 143A, usually lightly suffused on the very edge of the leaf with between 187A and 187B. The under surface color of the young leaf is between 146A and 146B, sometimes lightly suffused with between 187B and 183A.

The rachis is moderately heavy in caliper and rough. The upper side is deeply grooved with some hairs and few stipitate glands on the edges of the grooves. The under side of the rachis is rough with some hairs, few stipitate glands and small prickles. The rachis color is near 146C on the under side and near 137A on the upper side moderately suffused especially on the young leaf with between 187A and 187B.

The stipules are about 1.3 to about 2.0 cm. in length and moderately wide (about 0.6 to about 0.8 cm.) with long straight points that usually turn out at an angle of more than 45 degrees. The under and upper surface color of the stipule is between 139A and 137A sometimes lightly suffused especially on the young leaf with between 187C and 187D.

The petiole is moderately heavy in caliper and rough. The upper side is deeply grooved with some hairs and few stipitate glands on the edges of the grooves. The under side of the petiole is rough with some hairs, few stipitate glands and small prickles. The petiole is about 0.8 to about 1.8 cm. in length and about 0.1 to about 0.2 cm in diameter at the widest point. The petiole color is near 146C on the under side and near 137A on the upper side moderately suffused especially on the young leaf with between 187A and 187B.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has a spreading climbing growth habit with canes about 300 cm. to about 350 cm. in length with moderately full branching. It displays vigorous growth and the canes are of medium to somewhat light caliper for the class (about 1.3 to about 1.9 cm. in width at the widest point).

The color of the major stems is between 146C and 152A. They bear some large prickles that are about 0.8 to about 1.1 cm. in length. The large prickles are hooked moderately downward with a medium length somewhat narrow oval base; prickle color is between 165B and 164A. The major stem bears small prickles of similar shape and coloration.

The color of the branches is between 146A and 146B. They bear some large prickles which are of similar shape to the large prickles on the major stems. The prickles are about 0.4 to about 0.6 cm. in length. Prickle color is between 161A and 162A sometimes lightly blushed with near 187D. The branches bear few small prickles of similar shape and coloration.

The color of the new shoots is between 144A and 146B often moderately suffused with between 187A and 187B. They bear some large prickles which are of similar size and shape to the large prickles on the major stems; prickle color is between 152C and 153A often heavily suffused with between 187B and 187A. The shoots bear few small prickles of similar shape and coloration.

I claim:

1. A new and distinct Climbing rose plant of the variety substantially as described and illustrated herein.

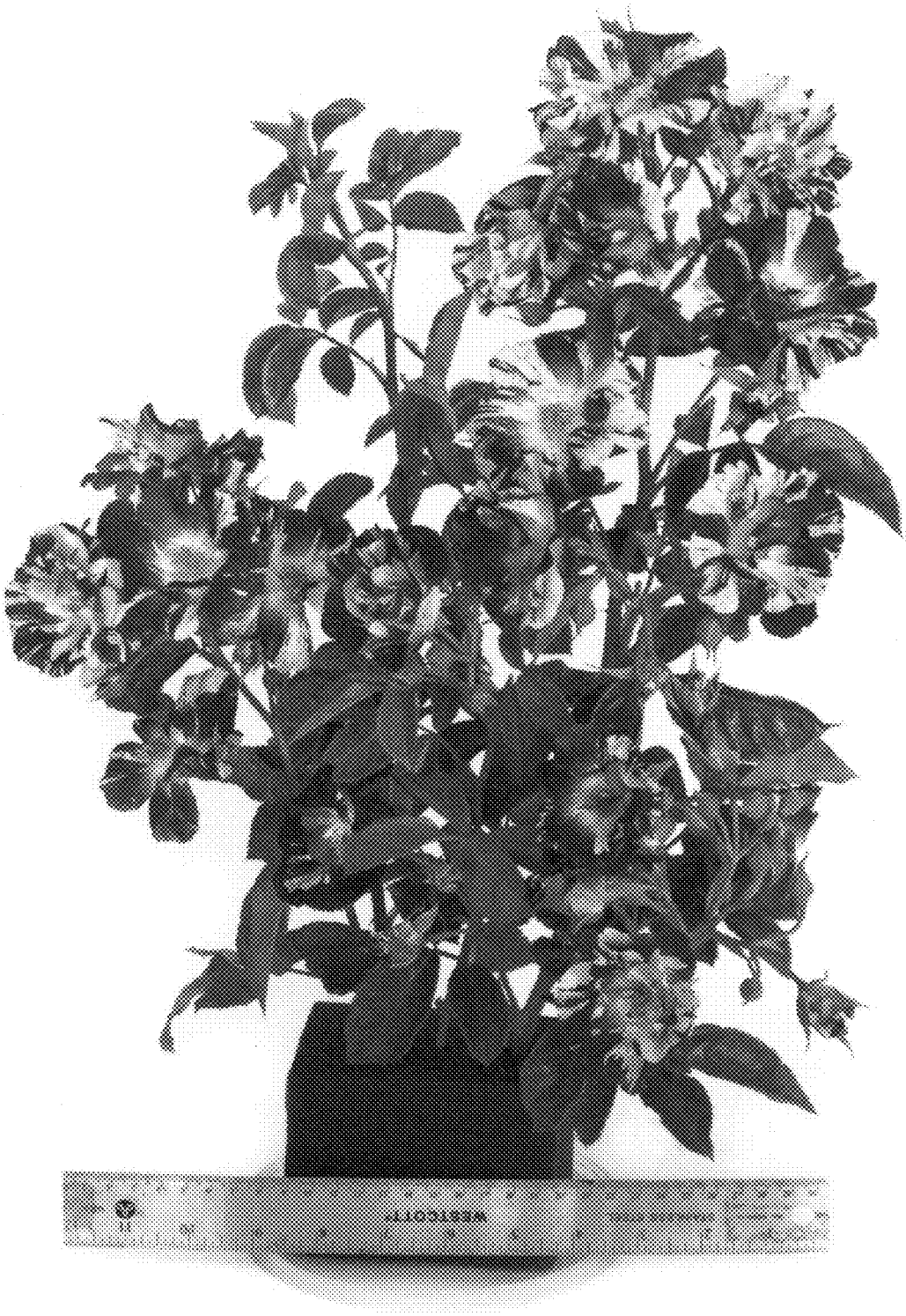

* * * * *